US008871508B2

(12) United States Patent
Radford et al.

(10) Patent No.: US 8,871,508 B2
(45) Date of Patent: Oct. 28, 2014

(54) CELL-MEDIATED IMMUNE RESPONSE ASSAY AND KITS THEREFOR

(75) Inventors: Anthony J. Radford, Southbank (AU); Stephen L. Jones, East Brunswick (AU); Jenny L. Howard, Bentleigh East (AU)

(73) Assignee: Cellestis Limited, Carnegie (AU)

( * ) Notice: Subject to any disclaimer, the term of this patent is extended or adjusted under 35 U.S.C. 154(b) by 121 days.

(21) Appl. No.: 12/531,288

(22) PCT Filed: Mar. 14, 2008

(86) PCT No.: PCT/AU2008/000377
§ 371 (c)(1),
(2), (4) Date: Mar. 23, 2010

(87) PCT Pub. No.: WO2008/113119
PCT Pub. Date: Sep. 25, 2008

(65) Prior Publication Data
US 2010/0221712 A1    Sep. 2, 2010

(30) Foreign Application Priority Data

Mar. 16, 2007 (AU) ............................... 2007901385

(51) Int. Cl.
*C12N 5/08* (2006.01)
*C12N 5/00* (2006.01)
*C12N 5/02* (2006.01)
*G01N 33/569* (2006.01)
*G01N 33/68* (2006.01)

(52) U.S. Cl.
CPC ...... *G01N 33/56972* (2013.01); *G01N 2333/57* (2013.01); *G01N 2333/35* (2013.01); *G01N 33/6863* (2013.01)
USPC ........................... 435/372; 435/373; 435/375

(58) Field of Classification Search
None
See application file for complete search history.

(56) References Cited

U.S. PATENT DOCUMENTS

| | | | | |
|---|---|---|---|---|
| 4,016,043 | A | 4/1977 | Schuurs et al. | 195/103.5 |
| 4,018,653 | A | 4/1977 | Mennen | 195/127 |
| 4,424,279 | A | 1/1984 | Bohn et al. | 436/534 |
| 4,469,110 | A | 9/1984 | Slama | 128/770 |
| 5,494,799 | A * | 2/1996 | Wood et al. | 435/7.32 |
| 7,608,392 | B2 * | 10/2009 | Rothel et al. | 435/5 |
| 2010/0167319 | A1 * | 7/2010 | Hope et al. | 435/7.92 |

FOREIGN PATENT DOCUMENTS

| WO | 2004/042396 | 5/2004 |
|---|---|---|
| WO | 2006/085897 | 8/2006 |

OTHER PUBLICATIONS

Altschul et al., "Gapped BLAST and PSI-BLAST: a new generation of protein database search programs," *Nucleic Acids Res.* 25(17):3389-3402, 1997.
Antas et al., "Whole Blood Assay to Access T Cell-immune Responses to *Mycobacterium tuberculosis* Antigens in Healthy Brazilian Individuals," *Mem Inst Oswaldo Cruz* 99(1):53-55, 2004.
Baird et al., "Dendritic cell presentation of PPD and 19 kDa protein of *Mycobacterium tuberculosis* and emgergent T helper cell phenotype," *Immunology and Cell Biology* 73:537-543, 1995.
Benyoucef et al., "An interferon-γ (IFN-γ) based whole blood assay to detect T cell response to antigens in HIV-1 infected patients," *Path Biol* 45(5):400-403, 1997.
Bigos et al., "Nine Color Eleven Parameter Immunophenotyping Using Three Laser Flow Cytometry," *Cytometry* 36:36-45, 1999.
Bonner et al., "A Film Detection Method for Tritium-Labelled Proteins and Nucleic Acids in Polyacrylamide Gels," *Eur. J. Biochem.* 46:83-88, 1974.
Brock et al., "Performance of whole blood IFN-γ test for tuberculosis diagnosis based on PPD or the specific antigens ESAT-6 and CFP-10," *Int J. Tuberc Lung Dis* 5(5):462-467, 2001.
Daneshvar et al., "Detection of biomolecules in the near-infrared spectral region via a fibor-optic immunosensor," *J. Immunol. Methods* 226:119-128, 1999.
Durig et al., "Fourier Transform Raman Spectroscopy of Brightly Colored Commercially Available Dyestuffs and Pigments," *Journal of Raman Spectroscopy* 24:281-285, 1993.
Erickson et al., "Design, Activity, and 2.8 Å Crystal Structure of a $C_2$ Symmetric Inhibitor Complexed to HIV-1 Protease," *Science* 249:527-533, 1990.
Fu et al., "A microfabricated fluorescence-activated cell sorter," *Nature Biotechnology* 17:1109-1111, 1999.
Hodgson, "Data-Directed Drug Design," *Bio/Technology* 9:19-21, 1991.
Kampmann et al., "Evaluation of Human Antimycobacterial Immunity Using Recombinant Reporter Mycobacteria," *The Journal of Infectious Diseases* 182:895-901, 2000.
Katial et al., "Cell-Mediated Immune Response to Tuberculosis Antigens: Comparison of Skin Testing and Measurement of In Vitro Gamma Interferon Production in Whole-Blood Culture," *Clinical and Diagnostic Laboratory Immunology* 8(2):339-345, 2001.
Kurrek, "Antisense technologies. Improvement through novel chemical modifications," *Eur. J. Biochem.* 270:1628-1644, 2003.
Lakowicz et al., "Time-Resolved Fluorescence Spectroscopy and Imaging of DNA Labeled with DAPI and Hoechst 33342 Using Three-Photon Excitation," *Biophys J.* 72:567-578, 1997.

(Continued)

*Primary Examiner* — Michail Belyavskyi
(74) *Attorney, Agent, or Firm* — Seed IP Law Group PLLC

(57) ABSTRACT

The present invention provides methods and kits for measuring a cell-mediated immune (CMI) in a small volume of whole undiluted blood collected from a subject. In particular, the methods are for measuring responses in undiluted whole blood samples having a volume of, for example, 50 µl to 500 µl. Thus, capillary sampling and rapid testing of subjects including pediatric, adult or geriatric human subjects are facilitated.

11 Claims, 2 Drawing Sheets

(56) References Cited

OTHER PUBLICATIONS

Lewis et al., "Erratum to "The use of Fourier Transform Infrared (FT-IR) spectroscopy to study the state of heterobifunctional reactive dyes" [Dyes and Pigments 1998; 39:111-123]," *Dyes Pigm.* 42:197, 1999.

Marmur et al., "Determination of the Base Composition of Deoxyribonucleic Acid from its Thermal Denaturation Temperature," *J. Mol. Biol.* 5:109-118, 1962.

Rahman et al., "Infrared and Raman Spectra of a Single Resin Bead for Analysis of Solid-Phase Reactions and Use in Encoding Combinatorial Libraries," *J. Org. Chem.* 63:6196-6199, 1998.

Rapaport et al., "Visible light emission from dyes excited by simultaneous absorption of two different frequency beams of light," *Applied Physics Letters* 74(3):329-331, 1999.

Skjot et al., "Comparative Evaluation of Low-Molecular-Mass Proteins from *Mycobacterium tuberculosis* Identifies Members of the ESAT-6 Family as Immunodominant T-Cell Antigens," *Infection and Immunity* 68(1):214-220, 2000.

Streeton et al., "Sensitivity and specificity of a gamma interferon blood test for tuberculosis infection," *Int J Tuberc Lung Dis* 2(6):443-450, 1998.

van Crevel et al., "Disease-specific ex vivo stimulation of whole blood for cytokine production: applications in the study of tuberculosis," *Journal of Immunological Methods* 222:145-153, 1999.

Wells, "Systematic Mutational Analyses of Protein-Protein Interfaces," *Methods in Enzymology* 202:390-411, 1991.

Whist et al., "The use of interleukin-2 receptor expression as a marker of cell-mediated immunity in goats experimentally infected with *Mycobacterium avium* ssp. *paratuberculosis*," *Veterinary Immunology and Immunopathology* 73:207-218, 2000.

\* cited by examiner

CELL-MEDIATED IMMUNE RESPONSE ASSAY AND KITS THEREFOR

FIELD

The present invention relates generally to methods and kits for use in diagnosis, monitoring or treatment that measure cellular responsiveness to an agent in vitro. In particular, the present invention provides a system for measuring a cell-mediated immune (CMI) response to an antigen in a small sample of whole blood collected from a subject. The methods and kits will find broad application in the analysis of whole blood samples having a range of different volumes including those from infants and children or other subjects where sample volume is limiting or where small sample volumes are desirable.

BACKGROUND

Bibliographic details of the publications referred to by author in this specification are collected at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The function of the immune response is to disarm invading pathogens or toxins. The immune response can in some circumstances be very destructive to an organism and survival depends upon the ability of the immune system to distinguish self from non-self. Autoimmune diseases, for example, develop when the immune system over responds to self. Some immune responses are against non-self molecules that are relatively harmless. Asthma and hayfever, for example, involve immune responses to non-self where the immune response is more debilitating than the causative agent. Generally, the innate immune system screens out responses to non-pathogenic organisms and helps to prevent adaptive immune responses to such harmless agents.

Adaptive immune responses are carried out by lymphocytes such as B lymphocytes that carry out antibody responses or T lymphocytes which carry out cell mediated responses. B lymphocytes produce immunoglobulins which help to deactivate pathogens and toxins. T cells react directly with non-self molecules (antigens) that are presented on the surface of host cells in association with major histocompatibility (MHC) molecules that provide a repertoire of "self" molecules. In both cases, a cellular response is generated that is specific to particular epitopes of the non-self molecule and provides a network of immune responses and immune effector molecules.

Accordingly, one method for diagnosing or monitoring an infection or evaluating the ability of a subject to mount an immune response to non-self is to determine whether the subject has mounted an immune response to antigen stimulation. As the T cell response comprises the production of effector T cells that are capable of responding to an antigen or can be stimulated to respond to the antigen by producing immune effector molecules, one can measure the production of these molecules in vitro in response to specific antigens as a measure of a cell mediated immune response. However, as non-self antigenic molecules are presented to T-cells by antigen presenting cells there is a complex interaction of molecules and cells that must take place successfully in vitro in order to produce sufficient immune effector molecule for detection.

Most in vitro methods for detecting cell mediated immune responses involve the purification of peripheral blood mononuclear cells from whole blood using various separation techniques. Such assays include chromium release assays, cytotoxicity assays, MHC class I tetramer assays, assays for IFN-γ or other cytokines, of which ELISPOT provides a good example. The ELISPOT method immobilizes antigen presenting cells and has been used to detect the number of T-cells producing certain cytokines in response to antigenic stimulation.

If whole blood is used, it is generally diluted in a culture medium in order to dilute red blood cells, which are considered to reduce the sensitivity of the assays. An in-tube cell-mediated immune response assay which uses undiluted whole blood is described in International Publication No. WO 2004/042396 in the name of Cellestis Limited incorporated herein in its entirety by reference. International Publication No. WO 2004/042396 discloses the use of blood collection tubes for the incubation of sample with antigen and a simple sugar and shows enhanced sensitivity using the tube system compared to assays where blood is transferred to and incubated in 24-well microtitre plates.

For whole blood assays in humans and livestock animals, at least about three milliliters of blood is taken from the subject in order to provide sufficient material to perform cell-mediated immune response assays. This amount is generally taken by venous blood sampling, via needle into a collection vessel, often under vacuum.

Various methods of detecting immune effector molecules, such as enzyme-linked immunosorbent assay (ELISA), radio-immuno assay (RIA), or cytometric methods can use small volumes, however, there is a need in the art for improved systems for conducting the antigenic stimulation phases of in vitro cell-mediated immune response assays. In particular, methods that allow whole blood testing in small volumes of blood such as those obtained by peripheral capillary sampling are needed. The ability to screen small samples of blood would greatly facilitate sampling of children or other subjects where blood may be limited or difficult to obtain, and allows blood sampling without venous blood sampling by using capillary blood such as that obtained by prick testing of the thumb, heel, ear-lobe or other convenient site, and for testing multiple or a range of antigen including mitogen and hapten stimulants in a single blood draw of low volume.

SUMMARY OF THE BROAD EMBODIMENTS

The present invention is predicated, in part, upon the surprising discovery that it is possible to generate and detect a cellular immune response in a very small volume of whole blood from a subject, and that this does not have to be venous or arterial blood. This means that collection of blood for the conduct of cell-mediated immune response assays can be achieved using, for example, prick sampling of peripheral capillary blood which generally yields volumes of about one milliliter or less. Further, that very small samples of whole blood can be tested for their ability to produce immune effector molecules, facilitating multiple testing from small samples.

In one broad embodiment, the present invention provides a method for measuring a cell-mediated immune response in a sample from a subject, wherein the sample comprises cells that secrete an immune effector molecule following stimulation by an agent such as an antigen. In one particular embodiment, the present invention provides a method for measuring a cell-mediated immune (CMI) response in a sample of whole blood collected from a subject wherein said whole blood sample comprises cells of the immune system which are capable of producing immune effector molecules following stimulation by an antigen, the method comprising: (i) incubating a whole blood sample from a peripheral capillary or less than 0.5 mL whole blood from a artery or vein of a subject with an antigen in an incubation container substantially without dilution of the sample; and (ii) detecting or measuring the presence of an immune effector molecule or of a nucleic acid molecule capable of producing an effector molecule indicative of the capacity of the subject to mount a cell-mediated response.

In another embodiment, the method comprises: (i) collecting a whole blood sample from a peripheral capillary or less than 0.5 mL whole blood from an artery or vein of a subject into a container; (ii) incubating whole blood with an antigen and anti-coagulant; and (iii) detecting or measuring the presence of an immune effector molecule or of a nucleic acid molecule capable of producing an immune effector molecule indicative of the capacity of the subject to mount a cell-mediated response.

The method will find broad application in selecting a suitable therapeutic protocol for the treatment of a subject having, for example, an inflammatory disease condition, a pathogenic infection such as one caused by a bacterial, viral, parasite or fungal pathogen, an autoimmune disorder, immuno-incompetence, allergy or cancer or a propensity for developing such a disorder.

In a preferred embodiment, the methods comprise collecting and/or incubating a capillary blood sample or collecting a sample from the subject with a capillary sampling device.

The method comprises, in some embodiments, incubating the sample with an agent under conditions in which the shape of the sample comprises a dimension which has been optimised. In some embodiments, the dimension has been optimised for a particular subject or subject population. In other embodiments, the dimension has been optimised for a particular cellular sample. In some embodiments, the dimension is the height of the sample. In another embodiment, the volume is optimised. In a further embodiment, the concentration of peripheral blood mononuclear cells (PBMC) or other immune cells is also optimised. By "optimised" is meant that the selected dimension value or range provides the optimal cellular response compared to other values or ranges tested. Thus, in some embodiments, the sample comprises a dimension that has been pre-selected using the methods disclosed herein to provide an optimal cellular response.

As illustrated in Example 1, standard conjugate-linked immunoassay testing demonstrated that IFN-γ is produced in total volumes of blood incubation as small as 0.5 mL, 0.4 mL, 0.3 mL, 0.2 mL and 0.1 mL. Further experiments, described in Examples 2 to 4 show that incubation of blood samples as small as 20 μl and/or having a sample height of 4 mm can generate sufficient immune effector molecules to be useful in a diagnostic assay. Optimum results are obtained in sample heights of about 6 mm to about 12 mm or about 5 mm to about 18 mm and intermediate values, independent of the volume of sample collected or incubated.

Accordingly, in some embodiments, the incubation container is suitable for maintaining an optimal shape of the sample, wherein the shape has one or two or more dimensions selected from: (i) a maximum circular diameter of less than about 6 mm; (ii) a height of at least about 4 mm to 6 mm to a maximum height of about 12 mm to 20 mm; or (iii) a volume of less than 0.5 mL and optionally less than about 400 μl.

In another aspect, the present invention provides a kit for measuring a cell mediated response to an agent in a whole blood sample from a subject, the kit comprising: a collection vessel housed separately or together with an agent capable of stimulating an immune cell to secrete an immune effector molecule, and further optionally comprising instructions for use. In some embodiments, the sample is transferred from a collection container to one or more containers for incubation with antigen and the kit comprises one or more collection container and one or more incubation container. Conveniently, in some embodiments, the collection container comprises anticoagulant. In other embodiments, the incubation container comprises antigen and optionally a simple sugar such as dextrose.

Accordingly, the present invention provides kits for measuring a cell-mediated immune response in a whole blood sample collected from a subject, the kits comprising in multicomponent form: (i) one or more collection and/or incubation containers suitable for holding or incubating a whole peripheral capillary blood sample or less than 0.5 mL of whole venous or arterial blood; (ii) one or more test antigens for analysis of in vitro responses thereto and optionally a control antigen; (iii) reagents for measuring the presence or elevation in the level of an immune effector molecule; and (iv) optionally a set of instructions comprising any of the herein disclosed methods.

In some embodiments, the incubation container is suitable for maintaining an optimal shape of the sample, wherein the shape has one or two or more dimensions selected from: (i) a maximum circular diameter of less than about 6 mm; (ii) a height of at least about 4 mm to 6 mm to a maximum height of about 12 mm to 20 mm; or (iii) a volume of less than 0.5 mL and optionally less than 400 μl.

Instructions, for example, may comprise instructions to collect whole blood and mix blood in collection/incubation container in order to mix anticoagulant with the blood. In other embodiments, the instructions include instructions to incubate the whole blood sample with an antigen and optionally with a control antigen or mitogen. In other embodiments, the instructions comprise instructions to centrifuge the incubation container and collect plasma. In some embodiments, the instructions comprise instructions to detect an immune effector molecule in plasma.

In some embodiments, the collection vessel is marked to identify a sample height of about 12 mm. In some embodiments, the kit comprises a plurality of marked collection vessels of the same and/or different dimensions. In some embodiments, the kit comprises a capillary sampling device. In another embodiment, the kit comprises one or more test antigens for diagnosis and optionally a mitogen as a control antigen for the analysis of in vitro responses thereto. Optionally, the kit further comprises reagents appropriate for measuring the presence or elevation in the level of an immune effector molecule or their encoding molecules, including positive and negative controls. In some embodiments, the kit further comprises reagents appropriate for the conduct of an assay for immune effector detection. In one embodiment, the assay is an assay for IFN-γ, or a downstream effector molecule. In a preferred embodiment, the reagent comprises an antibody conjugate for detecting IFN-γ, TNF or GM-CSF. In an exemplary embodiment the antibody conjugate detects IFN-γ. Such assays include, for example, an ELISA or ELISPOT based assay or similar assays known in the art. In another embodiment, the assay is a reverse transcription-amplification assay for RNA encoding the immune effector molecule, such as IFN-γ. Such assays are known in the art and are described for example, Sambrook, *Molecular Cloning: A Laboratory Manual*, 3rd Edition, CSHLP, CSH, NY, 2001 and Ausubel (Ed) *Current Protocols in Molecular Biology*, 5th Edition, John Wiley & Sons, Inc, NY, 2002.

In another aspect, the present invention contemplates methods which may be automated or semi-automated, computer programs, computer products, computers for facilitating the interpretation of output from the subject assays.

The above summary is not and should not been seen in any way as an exhaustive recitation of all embodiments of the present invention.

DETAILED DESCRIPTION OF THE PREFERRED EMBODIMENTS

Figure 1:
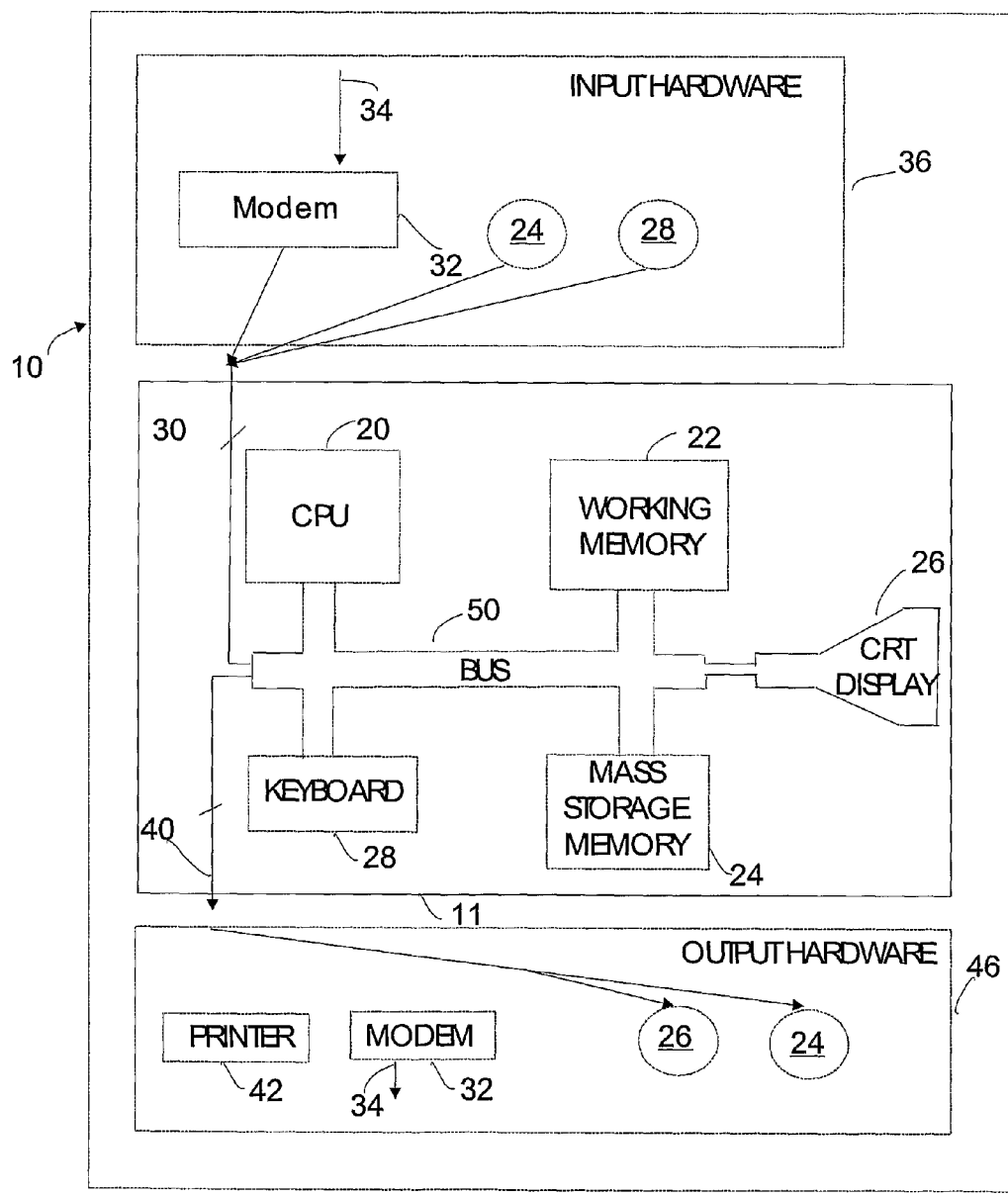
FIG. 1 is a diagrammatic representation of a system used to carry out the instructions encoded by the storage medium.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The term "about" provides for some variation or correction in the numerical value of the term which it precedes. It pertains to a quantity, volume, level, value, percentage, dimension, size or amount that varies by as much as 35%, 30%, 25%, 20%, 15%, 10%, 5%, 4% or 3% to a recited term. Thus, "at least about 6 mm" includes 4 mm or 5 mm as well as 6 mm and heights greater than 6 mm, while "about 12 mm" includes 13 mm, 14 mm, 15 mm or 16 mm and heights smaller than 12 mm. In addition, the term covers parts of unit numerical values, such as 6.5 mm or 6.9 mm etc. In a preferred embodiment, the variation is minor and is limited to a 10% or 15% variation in the numerical value.

The articles "a" and "an" are used herein to refer to one or to more than one (i.e. to at least one) of the grammatical object of the article. By way of example, "an antigen" means one antigen or more than one antigen, "an immune effector molecule" means one or more immune effector molecules.

The term "antigen" as used herein includes any molecule or agent that stimulates an immune response, and particularly a cellular immune response and includes an antisense protein or peptide, a hapten, mitogen, allergen or toxin or any naturally occurring or synthetic molecule or parts thereof having this activity. In some embodiments, the antigen comprises one or more full length or part length polypeptides. In other embodiments, the antigen comprises a peptide or a set of peptides from one or more different full length or part length polypeptides. In some embodiments, antigens are employed which mimic one or more of the effects of antigens presented to the immune system in vivo. Generally, test antigens are selected for optimum selectivity and sensitivity in a given population or subject. In one illustrative embodiment, the antigen is an antigen from *Mycobacterium tuberculosis*. In some embodiments, the antigen is a tuberculosis (TB)-specific antigen. In other embodiments, the antigen is purified protein derivative from *Mycobacterium ruberculosis* or *M. avium*. In some embodiments, the antigen simulates mycobacterial proteins such as ESAT-6 (Skjot et al., *Infection and Immunity*, 68(1):214-20, 2000), CFP-10 and TB7 (Brock et al., *Int. J. Tuberc. Lung. Dis*, 5(5):462-467, 2001). A mitogen may be used as a positive control or to detect the ability of cells in the sample to mount an antigen non-specific immune response. In other embodiments, the agent is a mitogen. In other embodiments, the antigen is selected from a self-antigen, an antigen from a pathogenic organism, a metal or inorganic molecule stimulating immune response, or a tumor antigen. In some embodiments, the agent (antigen) is a phospholipid, phosphoprotein or phospholipoprotein. In another illustrative embodiment, the antigen is from cytomegalovirus (CMV). In some embodiments, the antigen from a pathogenic organism is a bacterial, viral, parasite or fungal antigen or analog thereof.

Unless the context requires otherwise, the word "comprise", and variations such as "comprises" and "comprising", will be understood to imply the inclusion of a stated integer or step or group of integers or steps but not the exclusion of any other integer or step or group of integers or steps.

Each embodiment described herein is to be applied mutatis mutandis to each and every other embodiment unless specifically stated otherwise.

Preferably, the "subject" is human. The present invention contemplates, however, primates, livestock animals, companion animals and avian species as well as non-mammalian animals such as reptiles and amphibians. The assay has applications, therefore, in human, livestock, veterinary and wild life therapy, diagnosis and monitoring. In some embodiments, the human subject is selected from a group exhibiting a particular attribute or condition. In some embodiments, the subject is a pediatric, adult or geriatric subject. In some embodiments, the subject has or has had a pathogenic infection, an autoimmune disorder, or cancer, or is undergoing treatment for cancer, or has a propensity for developing such a condition, is immunocompromised or undergoing an inflammatory response. Once the subject has been evaluated including using the present methods and/or kits, they may then be treated, and, accordingly, methods encompassing diagnosis and treatment are also specifically contemplated.

Accordingly, the present invention provides any of the herein disclosed methods wherein the subject is human, including a pediatric, adult or geriatric subject. In other embodiments, the subject is an animal or bird, such as a livestock, racing, exotic, migratory animal or bird.

As stated above, one of the significant advantages of the present invention is the facility to conduct CMI assays using undiluted whole blood from a peripheral capillary. Accordingly, in some embodiments, the method comprises collecting a sample from the subject with a capillary sampling device. The device may be a prick device suitable for capillary sampling any peripheral capillary such as those of the thumb, finger, heel, toe, ear lobe etc. In some embodiments, the device comprises a capillary tube. A capillary tube or other narrow or conical container is useful to form a sample shape of optimum height with very small samples, such as those between about 20 µl to 50 µl and about 200 µl to 250 µl. In some embodiments, the incubation container is suitable for maintaining an optimal shape of the sample, wherein the shape has one or two or more dimensions selected from: (i) a circular diameter of less than 6 mm; (ii) a height of at least about 4 mm to 6 mm to a maximum height of about 12 mm to 20 mm; or (iii) a volume of less than 0.5 mL and optionally less than 400 µl. In some embodiments, the sample in the container has a height of at least about 6 mm to a maximum of about 12 mm. In some embodiments, the sample has a height of 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm or 20 mm or an intervening height. In other embodiments, the sample has a height of 6 mm, 7 mm, 8 mm, 9 mm, 10 mm, 11 mm or 12 mm or an intermediate height. Regarding the volume of the sample, in some embodiments, the total sample volume incubated is less than 500 µl, less than 400 µl, less than 300 µl less than 200 µl, less than 100 µl, or less than 50 µl. Where the sample is capillary blood the total sample volume incubated is selected from about 200 µl, 1500 µl, 1400 µl, 1300 µl, 1200 µl, 1100 µl, 900 µl, 800 µl, 700 µl, 600 µl, 500 µl, 400 µl, 300 µl, 200 µl, 100 µl, 50 µl or 40 µl or an intermediate volume. In some embodiments, the sample is collected into an about 3-4 mm diameter capillary tube.

Reference to "immune cells" includes cells such as lymphocytes including natural killer (NK) cells, T-cells, ($CD4^+$ and/or $CD8^+$ cells), B-cells, macrophages and monocytes, dendritic cells or any other cell which is capable of producing an effector molecule in response to direct or indirect antigen stimulation. Conveniently, the immune cells are lymphocytes and more particularly T-lymphocytes.

Accordingly, the present invention contemplates the methods as herein disclosed wherein the immune cells are selected from a natural killer (NK) cell, T-cell, B-cell, macrophage or monocyte. In a preferred embodiment the cells are T-cells.

The immune effector molecules may be any of a range of molecules which are produced in response to cell activation or stimulation by an antigen. Although an interferon (IFN) such as IFN-γ is a particularly useful immune effector molecule, others include a range of cytokines such as interleukins (IL), e.g. IL-2, IL-3 IL-4, IL-5, IL-10 or IL-12, tumor necrosis factor alpha (TNF-α, TNF-β), a colony stimulating factor (CSF) such as granulocyte (G)-CSF or granulocyte macrophage (GM)-CSF amongst many others such as complement or components in the complement pathway, perforins, defensins, cathelicidins, granzymes, Fas ligand, CD-40 ligand, exotaxins, cytotoxins, chemokines and monokines.

Accordingly, in some embodiments the present invention provides methods wherein the immune effector molecule is a cytokine, component of the complement system, perforin, defensin, cathelicidin, granzyme, Fas ligand, CD-40 ligand, exotaxin, cytotoxin, chemokine or monokine. In a preferred embodiment, the cytokine is IFN-γ, TNFα or GM-CSF.

By "whole blood" is meant blood from a subject that has not been substantially diluted or fractionated, maintaining the ambient environment of blood for the cells as close to natural plasma conditions as practical. Thus the addition of small volumes or dried amounts of, for example antigen, sugar or anticoagulant does not constitute dilution in accordance with the present invention, whereas addition of culture medium in excess of the blood volume constitutes dilution. Notwithstanding that whole undiluted blood is the preferred and most convenient sample, the present invention extends to other samples containing immune cells such as lymph fluid, cerebral, fluid, tissue fluid (such as bone marrow or thymus fluid) and respiratory fluid including nasal and pulmonary fluid. Derivatives of these samples may also be obtained by processing. For example, buffy coat cells or peripheral blood mononuclear cells or antigen processing cells are obtained by methods known in the art. Whole blood may also be treated to remove components such as red blood cells and/or platelets by methods known in the art. Substantial dilution would occur by the addition to the sample of more than about 40% to 50% of the original volume.

Accordingly, in some embodiments, the method comprises detecting the presence of an effector molecule or a nucleic acid molecule capable of producing an effector molecule. In this embodiment, the presence or an elevation in the level of a effector molecule or a nucleic acid molecule capable of producing the effector molecule is indicative of the capacity of the subject to mount a cell-mediated response.

In an illustrative embodiment, the shape of the sample comprises a height which has been optimised. In one example of this embodiment, the cellular sample comprises a height of at least 6 milliliters (mm) to a maximum of about 12 mm or any intervening height. As the skilled artisan will appreciate, the presently disclosed requirement for an optimised height for the sample permits considerable variation or choice concerning the volume of sample employed and the shape of the container in which the sample is incubated. Thus, in some embodiments, a large volume of sample, say 10 milliliters (mL) of blood is incubated in a container of appropriate dimensions to ensure that the height of the sample during incubation does not exceed about 12 mm. At the other end of scale, a 50 microliter (µl) sample could be incubated, for example, in a 3-4 mm diameter capillary tube in order to provide a sample height of at least about 6 mm to a maximum of about 12 mm or any intervening height. The present invention is not necessarily limited to any particular volume of sample to be incubated or to any particular dimension or shape of sample containing vessel. However, it is a preferred aspect that the present invention facilitates the use of small volumes of blood (including capillary sampling volumes) and therefore avoids the need for venous blood sampling. Further, that there is no need to dilute blood, requiring further handling steps and maintains the blood in its optional state for measuring an immune response. The above optimum heights have been determined using whole blood from human donors. Other subjects or subject populations or subgroups or cellular sample types have different features and exhibit some variation in the optimum height for sample incubation. In these groups some further minor variation in the minimum and maximum height for sample incubation through optimisation is contemplated. Once the present invention is appreciated, such optimisation is well within the skill of the addressee.

In some embodiments, the container in which sample and antigen are co-incubated is also the collection container used to collect sample from the subject. Any one of a large number of different available containers may be used provided that they provide suitable sample dimensions. A number of different tubes are described in the Examples for the purpose of illustration and the present invention is in no way restricted to these containers. In some embodiments, the container is a tube which comprises a vacuum to facilitate the collection of blood from a subject. In other embodiments, the container is a capillary tube. In some embodiments, a capillary tube is used to collect blood from the surface of the skin by capillary action. In some embodiments, the sample is collected from a subject into a collection container containing antigen or to which antigen is subsequently added. In some embodiments, the blood is sampled using a capillary sampling device such as a pin prick device and blood is collected into a heparinised collecting container and subsequently transferred into an appropriate container for co-incubation with agent.

In some embodiments, the sample is a blood sample. Generally, blood is maintained in the presence of an anticoagulant such as heparin which may be in the container when blood is added or is added subsequently. Optionally, a simple sugar such as dextrose is contained in the container or added to the incubation mixture. In some preferred embodiments, the blood sample is a whole blood sample. In some embodiments, whole blood from a subject is collected into a container containing antigen and/or anti-coagulant, in other embodiments, antigen and/or anti-coagulant are added to the blood thereafter.

In one embodiment, the method comprises: collecting a blood sample from a subject using a capillary sampling device and introducing blood into a suitable collection vessel. In some embodiments, the capillary sampling device comprises an anticoagulant and the antigen. In other embodiments, the collection vessel or subsequent vessel comprises the antigen. In other embodiments, the collection vessel comprises a simple sugar such as dextrose or other agent that maintains the ability of the sample cells to mount a CMI response. By whatever route, the method comprises contacting the antigen with the blood sample substantially without dilution of the sample and incubating the sample with the antigen under conditions in which the shape of the sample comprises a height that has been optimised for a particular subject or subject population or sample type. In another embodiment, the method comprises incubating the sample with the agent and detecting the presence of an effector molecule or a nucleic acid molecule capable of producing an effector molecule. In an illustrative embodiment, the immune effector molecule is a cytokine such as IFN-γ.

In other embodiments, blood is collected by standard procedures into a collection vessel and transferred to sample (testing) vessels of pre-determined dimensions to ensure that a defined volume of blood is incubated with the antigen under conditions in which the shape of the sample comprises a height or volume that has been optimised for a particular subject or subject population or sample type.

The use of blood collection tubes as collection vessels and testing vessels is disclosed in International Publication No. WO 2004/042396 in the name of Cellestis Limited the content of which is incorporated herein in its entirety by reference.

In some embodiments, the blood sample incubated with an antigen comprises a volume of less than about 1 mL of blood or more than about 2 mL of blood. In other embodiments, the 1 mL blood sample or about 1 mL blood sample during incubation does not comprise a breadth of 13 mm.

In some embodiments, the capillary sampling device is a prick device, such as, but by no means limited to those described in U.S. Pat. No. 4,469,110.

In another embodiment, the method comprises evaluating a cell-mediated immune response in a blood sample from one or more subject groups wherein samples from each subject group are evaluated to determine a minimum volume of sample to be assessed from each subject group. Optionally, the method comprises sampling the amount of blood appropriate to each subject or subject group wherein each sample comprises, during incubation with antigens, a shape comprising a height that has been optimised for a particular subject or subject population or sample type. In this way, for example, the results from the analysis of subject samples comprising small sample volumes (less than about one milliliter) can readily be compared with the results from larger samples comprising, for example, several milliliters of blood. Thus, the present invention, by characterising and controlling a variable in the cell-mediated response assay, enhances the diagnostic value of the output from the assay.

The present invention is also predicated, in part, upon the observation that the height of the sample during incubation, determined by the shape of the incubation vessel, can be used to modulate the sensitivity of cell-mediated immune response assays. In one embodiment, the present invention provides a method of measuring a cell-mediated immune response in a cellular sample, said method comprising: incubating the sample with an antigen under conditions in which the shape of the sample comprises a height of at least 6 milliliters (mm) to about 12 mm. In a particularly useful application of this observation, the present invention provides a method of assaying samples from subjects where sample volume is limiting or where low sample volumes are desirable. In accordance with one embodiment of the present invention practiced with blood samples, blood samples as small as about 20 µl to about 200 µl are employed, wherein the shape of the sample during incubation comprises a height of at least about 6 milliliters (mm) at its highest point to a maximum height of about 12 mm at its highest point.

Accordingly, in one aspect the present invention provides a method of performing a cell mediated immune response assay on a sample from a subject wherein said method avoids the use of needles, the method comprising collecting blood using a capillary sampling device to take small volumes of blood. In another related aspect, the invention encompasses the practise of the herein described assays including the use of small volumes of sample such as one or more samples of about 20 µl to less than but about 1 mL. In other embodiments, standard blood sampling for cellular assay techniques are employed and larger sample volumes are used, typically 1 mL to 5 mL but encompassing volumes as great as about 10 to 200 mLs or more. In a preferred embodiment, the total incubation volume of whole blood is within the range of about 50 µl to less than about 500 µl.

The present invention provides a method for measuring a cell mediated immune (CMI) response in a subject sample comprising incubating the sample with an agent under conditions in which the shape of the sample comprises a dimension which has been optimised. In some embodiments, the cellular sample is incubated with the antigen for from about 4 or 5 to about 50 hours.

In some embodiments, the method is based upon measuring immune effector molecule production by cells of the immune system in response to antigenic stimulation. In other embodiments, immune effector molecule is the immediate effector molecule produced by effector T cells in response to antigen stimulation. In other embodiments, a downstream effector is measured. For example, IFN-γ or other immediate effector molecules elicit the production of further effector molecules whose production is measured. In another embodiment, the production of immune effectors is measured by measuring the level or presence of nucleic acid molecules capable of producing immune effectors. Accordingly, in some embodiments, immune effectors may be detected using ligands or binding molecules such as antibodies specific for the effectors or by measuring the level of expression of genes encoding the effectors. The present invention provides, therefore, a means to determine the cellular responsiveness of a subject and, in turn, provides a means for the diagnosis of infectious diseases, pathological conditions, immune status, level of immunocompetence and a marker of T-cell responsiveness to endogenous or exogenous antigens.

Accordingly, in another embodiment, the present invention contemplates a method for measuring a CMI response in a subject, said method comprising i) collecting a fluid sample from the subject into a collection vessel wherein said sample comprises cells of the immune system which produce immune effector molecules following stimulation by an agent. In some embodiments, the collection vessel comprises an anticoagulant, such as heparin. In other embodiments, the collection vessel comprises the agent. In some embodiments, the method further comprises contacting the agent with the sample in the collection vessel. The method further comprises iii) incubating said sample with an antigen under conditions in which the shape of the sample comprises a dimension which has been optimised. In some embodiments, the method optionally comprises iv) detecting the presence of an immune effector molecule or a nucleic acid molecule capable of producing either of these, wherein presence or elevation in the level of a effector molecule or a nucleic acid molecule capable of producing the effector molecule is indicative of the capacity of the subject to mount a cell-mediated response. In other embodiments, the immune effector is a cytokine, cytotoxin or chemokine. In an illustrative embodiment, the immune effector is IFN-γ.

In some embodiments, the shape of the sample is optimised by measuring effector cell function in samples having a range of dimensions and selecting the shape that is associated with the most sensitive measurement of effector cell function. In a preferred embodiment, the height of the sample is varied. In an illustrative embodiment, the height of the sample is varied about 12 mm for a maximum height and about 6 mm for a minimum height.

According to a preferred embodiment the present invention provides a method for measuring a CMI response in a human subject, said method comprising collecting a sample from said human subject using a capillary sampling device into a collection vessel.

In some embodiments, the sample comprises cells of the immune system which are capable of producing immune effector molecules following stimulation by an antigen, mitogen or hapten. In some embodiments, the method comprises incubating said sample with an antigen and then measuring the presence of or elevation in the level of an immune effector molecule wherein the presence or level of said immune effector molecule is indicative of the capacity of said human subject to mount a cell-mediated immune response.

Accordingly, in another preferred embodiment, the present invention provides a method for measuring a CMI response in a subject, said method comprising collecting a sample from said subject into a collection vessel wherein said sample comprises cells of the immune system which are capable of producing IFN-γ molecules following stimulation by an antigen, incubating said sample with an antigen and then measuring the presence of or elevation in the level of an IFN-γ molecule wherein the presence or level of said IFN-γ molecule is indicative of the capacity of said subject to mount a cell-mediated immune response.

The sample collected from the subject is generally deposited into a blood collection vessel. Notwithstanding that whole undiluted blood is the preferred and most convenient sample, the present invention extends to other samples containing immune cells such as lymph fluid, cerebral, fluid, tissue fluid and respiratory fluid including nasal and pulmonary fluid.

The cells of the CMI system lose the capacity to mount a CMI response in whole blood after extended periods following blood draw from the subject, and responses without intervention are often severely reduced or absent by 24 hours following blood draw. The reduction of labor and need for specialized equipment in the present invention allows CMI stimulation with antigens to be performed at the point of care locations such as physicians' offices, clinics, outpatient facilities and veterinary clinics or on farms. Once antigen stimulation is complete, the requirement for fresh and active cells no longer exists. IFN-γ and other cytokines or immune effector molecules are stable in plasma and, thus, the sample can be stored, or shipped without special conditions or rapid time requirements in a similar fashion to standard serum samples used for other infectious disease or other disease diagnosis.

The incubation step may be from about 4 or 5 hours to 50 hours, more preferably about 5 hours to 40 hours and even more preferably about 8 to 24 or about 16 to 24 hours or a time period in between. In some embodiments, after an optional initial mixing step to distribute antigens throughout the sample, the sample incubating is carried out without mixing further.

Accordingly, another preferred embodiment of the present invention contemplates a method for measuring a CMI response in a subject including a human subject, said method comprising collecting a sample of whole blood from said subject by capillary sampling, incubating said whole blood sample with an antigen and then measuring the presence or elevation in level of an immune effector molecule such as IFN-γ wherein the presence or level of said immune effector molecule is indicative of the capacity of said subject to mount a cell-mediated immune response.

The ability to measure CMI is important for assessing a subject's ability to respond to an infection by an pathogenic agent such as a microorganism or virus or parasite, to mount an autoimmune response such as in diabetes to protect against cancers or other oncological conditions or to test for sensitivity to environmental antigens (allergy testing). Consequently, reference to "measuring a CMI response in a subject" includes and encompasses immune diagnosis of infectious and autoimmune diseases, a marker for immunocompetence and the detection of T-cell responses to endogenous and/or exogenous antigens (including a measure of the efficacy of a vaccine) as well as a marker for allergies, inflammatory diseases and cancer.

The ability to perform this test in small volumes of blood is important for pediatric and other samples where blood may be limiting. The absence of any handling steps in purifying lymphocytes adds an advantage in small blood volumes as purification and enumeration of lymphocytes from small volumes has practical difficulties, as does the addition of warmed sterile media and reagents in a sterile environment. The ability to obtain an optimal CMI response in a small volume by adjusting the relative proportions (such as, shape, width and height) of the incubating vessel or sample provides valuable advantages. The terms vessel, container, compartment are used interchangeably and include any receptacle that holds any volume, such as a well, dip, tube, eppendorf and the like.

Autoimmune diseases contemplated herein include inter alia Alopecia Areata, Ankylosing Spondylitis, Antiphospholipid Syndrome, Autoimmune Addison's Disease Multiple Sclerosis, Autoimmune disease of the adrenal gland, Autoimmune Hemolytic Anemia, Autoimmune Hepatitis, Autoimmune oophoritis and orchitis, Behcet's Disease, Bullous Pemphigoid, Cardiomyopathy, Celiac Sprue-Dermatitis, Chronic Fatigue Syndrome (CFIDS), Chronic Inflam. Demyelinating, Chronic Inflam. Polyneuropathy, Churg-Strauss Syndrome, Cicatricial Pemphigoid, CREST Syndrome, Cold Agglutinin Disease, Crohn's Disease, Dermatitis herpetiformis, Discoid Lupus, Essential Mixed Cryoglobulinemia, Fibromyalgia, Glomerulonephritis, Grave's Disease, Guillain-Barre, Hashimoto's Thyroiditis, Idiopathic Pulmonary Fibrosis, Idiopathic Thrombocytopenia Purpura (ITP), IgA Nephropathy Insulin Dependent Diabetes (Type I), Lichen Planus, Lupus, Meniere's Disease, Mixed Connective Tissue Disease, Multiple sclerosis, Myasthenia Gravis, Myocarditis, Pemphigus Vulgaris, Pernicious Anemia, Polyarteritis Nodosa, Polychondritis, Polyglancular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjogren's Syndrome, Stiff-Man Syndrome, Systemic lupus erythematosus, Takayasu Arteritis, Temporal Arteritis/Giant Cell Arteritis, Ulcerative Colitis, Uveitis, Vasculitis and Vitiligo.

It is generally important to assess the potential or actual CMI responsiveness in these individuals.

Other disease conditions contemplated include inflammatory disease conditions.

Examples of inflammatory disease conditions contemplated by the present invention include but are not limited to those disease and disorders which result in a response of redness, swelling, pain, and a feeling of heat in certain areas that is meant to protect tissues affected by injury or disease. Inflammatory diseases which can be treated using the methods of the present invention, include, without being limited to, acne, angina, arthritis, aspiration pneumonia, disease, empyema, gastroenteritis, inflammation, intestinal flu, NEC, necrotizing enterocolitis, pelvic inflammatory disease, pharyngitis, HD, pleurisy, raw throat, redness, rubor, sore throat, stomach flu and urinary tract infections, Chronic Inflammatory Demyelinating Polyneuropathy, Chronic Inflammatory Demyelinating Polyradiculoneuropathy, Chronic Inflammatory Demyelinating Polyneuropathy, Chronic Inflammatory Demyelinating Polyradiculoneuropathy.

Cancer therapy also is somewhat dependent on CMI. Cancers contemplated herein include: a group of diseases and disorders that are characterized by uncontrolled cellular growth (e.g. formation of tumor) without any differentiation of those cells into specialized and different cells. Such diseases and disorders include ABL1 protooncogene, AIDS Related Cancers, Acoustic Neuroma, Acute Lymphocytic Leukaemia, Acute Myeloid Leukaemia, Adenocystic carcinoma, Adrenocortical Cancer, Agnogenic myeloid metaplasia, Alopecia, Alveolar soft-part sarcoma, Anal cancer, Angiosarcoma, Aplastic Anaemia, Astrocytoma, Ataxia-telangiectasia, Basal Cell Carcinoma (Skin), Bladder Cancer, Bone Cancers, Bowel cancer, Brain Stem Glioma, Brain and CNS Tumours, Breast Cancer, CNS tumours, Carcinoid Tumours, Cervical Cancer, Childhood Brain Tumours, Childhood Cancer, Childhood Leukaemia, Childhood Soft Tissue Sarcoma, Chondrosarcoma, Choriocarcinoma, Chronic Lymphocytic Leukaemia, Chronic Myeloid Leukaemia, Colorectal Cancers, Cutaneous T-Cell Lymphoma, Dermatofibrosarcoma-provesselrans, Desmoplastic-Small-Round-Cell-Tumour, Ductal Carcinoma, Endocrine Cancers, Endometrial Cancer, Ependymoma, Esophageal Cancer, Ewing's Sarcoma, Extra-Hepatic Bile Duct Cancer, Eye Cancer, Eye: Melanoma, Retinoblastoma, Fallopian Vessel cancer, Fanconi Anaemia, Fibrosarcoma, Gall Bladder Cancer, Gastric Cancer, Gastrointestinal Cancers, Gastrointestinal-Carcinoid-Tumour, Genitourinary Cancers, Germ Cell Tumours, Gestational-Trophoblastic-Disease, Glioma, Gynaecological Cancers, Haematological Malignancies, Hairy Cell Leukaemia, Head and Neck Cancer, Hepatocellular Cancer, Hereditary Breast Cancer, Histiocytosis, Hodgkin's Disease, Human Papillomavirus, Hydatidiform mole, Hypercalcemia, Hypopharynx Cancer, IntraOcular Melanoma, Islet cell cancer, Kaposi's sarcoma, Kidney Cancer, Langerhan's-Cell-Histiocytosis, Laryngeal Cancer, Leiomyosarcoma, Leukaemia, Li-Fraumeni Syndrome, Lip Cancer, Liposarcoma, Liver Cancer, Lung Cancer, Lymphedema, Lymphoma, Hodgkin's Lymphoma, Non-Hodgkin's Lymphoma, Male Breast Cancer, Malignant-Rhabdoid-Tumour-of-Kidney, Medulloblastoma, Melanoma, Merkel Cell Cancer, Mesothelioma, Metastatic Cancer, Mouth Cancer, Multiple Endocrine Neoplasia, Mycosis Fungoides, Myelodysplastic Syndromes, Myeloma, Myeloproliferative Disorders, Nasal Cancer, Nasopharyngeal Cancer, Nephroblastoma, Neuroblastoma, Neurofibromatosis, Nijmegen Breakage Syndrome, Non-Melanoma Skin Cancer, Non-Small-Cell-Lung-Cancer-(NSCLC), Ocular Cancers, Oesophageal Cancer, Oral cavity Cancer, Oropharynx Cancer, Osteosarcoma, Ostomy Ovarian Cancer, Pancreas Cancer, Paranasal Cancer, Parathyroid Cancer, Parotid Gland Cancer, Penile Cancer, Peripheral-Neuro-ectodermal-Tumours, Pituitary Cancer, Polycythemia vera, Prostate Cancer, Rare-cancers-and-associated-disorders, Renal Cell Carcinoma, Retinoblastoma, Rhabdomyosarcoma, Rothmund-Thomson Syndrome, Salivary Gland Cancer, Sarcoma, Schwannoma, Sezary syndrome, Skin Cancer, Small Cell Lung Cancer (SCLC), Small Intestine Cancer, Soft Tissue Sarcoma, Spinal Cord Tumours, Squamous-Cell-Carcinoma-(skin), Stomach Cancer, Synovial sarcoma, Testicular Cancer, Thymus Cancer, Thyroid Cancer, Transitional-Cell-Cancer-(bladder), Transitional-Cell-Cancer-(renal-pelvis-/- ureter), Trophoblastic Cancer, Urethral Cancer, Urinary System Cancer, Uroplakins, Uterine sarcoma, Uterus Cancer, Vaginal Cancer, Vulva Cancer, Waldenstrom's-Macroglobulinemia, Wilms' Tumour.

Any of a range of antigens may be tested such as those specific for a particular organism, virus, autoantigen or cancer cell. Alternatively, more general agents may be used to test generic capacity of a cell-mediated immune response. Examples of the latter include PPD from *M. tuberculosis* and tetanus toxoid. Any peptide, polypeptide or protein, carbohydrate, glycoprotein, phospholipid, phosphoprotein or phospholipoprotein or non-protein chemical agent may be used in the present assay system.

As stated above, detection of the immune effector molecules may be made at the protein or nucleic acid levels. Consequently, reference to "presence or level of said immune effector molecule" includes direct and indirect data. For example, high levels of IFN-γ mRNA is indirect data showing increased levels of IFN-γ. Assays known in the art for assessing RNA are described for example in Sambrook, *Molecular Cloning: A Laboratory Manual*, $3^{rd}$ Edition, CSHLP, CSH, NY, 2001 and Ausubel (Ed) *Current Protocols in Molecular Biology*, $5^{th}$ Edition, John Wiley & Sons, Inc, NY, 2002.

Ligands to the immune effectors are particularly useful in detecting and/or quantitating these molecules. Antibodies to the immune effector molecules are particularly useful. Techniques for the assays contemplated herein are known in the art and include, for example, sandwich assays, ELISA and ELISPOT. Rapid point of care immunochromatographic devices are also included. Reference to "antibodies" includes parts of antibodies, mammalianized (e.g. humanized) antibodies, recombinant or synthetic antibodies and hybrid and single chain antibodies.

Both polyclonal and monoclonal antibodies are obtainable by immunization with the immune effectors or antigenic fragments thereof and either type is utilizable for immunoassays. The methods of obtaining both types of sera are well known in the art. Polyclonal sera are less preferred but are relatively easily prepared by injection of a suitable laboratory animal with an effective amount of the immune effector, or antigenic part thereof, collecting serum from the animal and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates, therefore, a method for detecting an immune effector in a sample comprising immune cells from a subject, said method comprising contacting said sample or an aliquot of said sample with an antibody specific for said immune effector or antigenic fragment thereof for a time and under conditions sufficient for an antibody-effector complex to form, and then detecting said complex.

A sample includes whole blood. This method includes micro-arrays and macro-arrays on planar or spherical solid supports.

A wide range of immunoassay techniques are available as can be seen by reference to U.S. Pat. Nos. 4,016,043, 4,424, 279 and 4,018,653.

The following is a description of one type of assay. An unlabeled antibody is immobilized on a solid substrate and the sample to be tested for the immune effectors (e.g. antigens) brought into contact with the bound molecule. After a suitable period of incubation, for a period of time sufficient to allow formation of an antibody-antigen complex, a second antibody specific to the antigen, labeled with a reporter molecule capable of producing a detectable signal, is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of antigen. This generalized technique is well known to those skilled in the art as would be any of a number of variations.

In these assays, a first antibody having specificity for the instant immune effectors is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of vessels, beads, spheres, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-120 minutes or where more convenient, overnight) and under suitable conditions (e.g. for about 20° C. to about 40° C.) to allow binding of any subunit present in the antibody. Following the incubation period, the antibody subunit solid phase is washed and dried and incubated with a second antibody specific for a portion of the antigen. The second antibody is linked to a reporter molecule which is used to indicate the binding of the second antibody to the hapten.

There are many variations to this assay. One particularly useful variation is a simultaneous assay where all or many of the components are admixed substantially simultaneously.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. Examples of suitable fluorophores are provided in Table 2. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-antigen complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. Again, the present invention extends to a substantially simultaneous assay.

Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic colour visually detectable with a light microscope. The fluorescent labeled antibody is allowed to bind to the first antibody-antigen complex. After washing off the unbound reagent, the remaining tertiary complex is then exposed to the light of the appropriate wavelength the fluorescence observed indicates the presence of the antigen of interest. Immunofluorescence and EIA techniques are both very well established in the art and are particularly preferred for the present method. However, other reporter molecules, such as radioisotope, chemiluminescent or bioluminescent molecules, may also be employed.

There are a range of other detection systems which may be employed including colloidal gold and all such detection systems are encompassed by the present invention.

The present invention also contemplates genetic assays such as involving RT-PCR analysis or other amplification based strategies known in the art to detect RNA expression products of a genetic sequence encoding an immune effector.

In one embodiment, PCR is conducted using pairs of primers, one or both of which are generally labeled with the same or a different reporter molecule capable of giving a distinguishable signal. The use of fluorophores is particularly useful in the practice of the present invention. Examples of suitable fluorophores may be selected from the list given in Table 2. Other labels include luminescence and phosphorescence as well as infrared dyes. These dyes or fluorophores may also be used as reporter molecules for antibodies.

Any suitable method of analyzing fluorescence emission is encompassed by the present invention. In this regard, the invention contemplates techniques including but not restricted to 2-photon and 3-photon time resolved fluorescence spectroscopy as, for example, disclosed by Lakowicz et al., *Biophys. J.*, 72: 567, 1997, fluorescence lifetime imaging as, for example, disclosed by Eriksson et al., *Biophys. J.*, 2:64, 1993 and fluorescence resonance energy transfer as, for example, disclosed by Youvan et al., *Biotechnology*. 3:1-18, 1997.

Luminescence and phosphorescence may result respectively from a suitable luminescent or phosphorescent label as is known in the art. Any optical means of identifying such label may be used in this regard.

Infrared radiation may result from a suitable infrared dye. Exemplary infrared dyes that may be employed in the invention include but are not limited to those disclosed in Lewis et al., *Dyes Pigm.*, 42(2):197, 1999, Tawa et al., *Mater. Res. Soc. Symp. Proc.*, 488

[Electrical, Optical and Magnetic Properties of Organic Solid-State Materials IV], 885-890, Daneshvar et al., *J. Immunol. Methods*, 226(1-2):119-128, 1999, Rapaport et al., *Appl. Phys. Lett.*, 74(3):329-331, 1999 and Durig et al., *J. Raman Spectrosc.*, 24(5):281-285, 1993. Any suitable infrared spectroscopic method may be employed to interrogate the infrared dye. For instance, fourier transform infrared spectroscopy as, for example, described by Rahman et al., *J. Org. Chem.*, 63:6196, 1998 may be used in this regard.

Suitably, electromagnetic scattering may result from diffraction, reflection, polarization or refraction of the incident electromagnetic radiation including light and X-rays. Such scattering can be used to quantitate the level of mRNA or level of protein.

Flow cytometry is particularly useful in analyzing fluorophore emission.

As is known in the art, flow cytometry is a high throughput technique which involves rapidly analyzing the physical and chemical characteristics of particles (e.g. labeled mRNA, DNA or proteins) as they pass through the path of one or more laser beams while suspended in a fluid stream. As each particle intercepts the laser beam, the scattered light and fluorescent light emitted by each cell or particle is detected and recorded using any suitable tracking algorithm as, for example, described hereunder.

A modern flow cytometer is able to perform these tasks up to 100,000 cells/particles $s^{-1}$. Through the use of an optical array of filters and dichroic mirrors, different wavelengths of fluorescent light can be separated and simultaneously detected. In addition, a number of lasers with different excitation wavelengths may be used. Hence, a variety of fluorophores can be used to target and examine, for example, different immune effectors within a sample or immune effectors from multiple subjects.

Suitable flow cytometers which may be used in the methods of the present invention include those which measure five to nine optical parameters (see Table 3) using a single excitation laser, commonly an argon ion air-cooled laser operating at 15 mW on its 488 nm spectral line. More advanced flow cytometers are capable of using multiple excitation lasers such as a HeNe laser (633 nm) or a HeCd laser (325 nm) in addition to the argon ion laser (488 or 514 nm).

For example, Biggs et al., *Cytometry*, 36:36-45, 1999 have constructed an 11-parameter flow cytometer using three excitation lasers and have demonstrated the use of nine distinguishable fluorophores in addition to forward and side scatter measurements for purposes of immunophenotyping (i.e. classifying) particles. The maximum number of parameters commercially available currently is 17: forward scatter, side scatter and three excitation lasers each with five fluorescence detectors. Whether all of the parameters can be adequately used depends heavily on the extinction coefficients, quantum yields and amount of spectral overlap between all fluorophores (Malemed et al., "*Flow cytometry and sorting*", $2^{nd}$ Ed., New York, Wiley-Liss, 1990). However, it will be understood that the present invention is not restricted to any particular flow cytometer or any particular set of parameters. In this regard, the invention also contemplates use in place of a conventional flow cytometer, a microfabricated flow cytometer as, for example, disclosed by Fu et al., *Nature Biotechnology*, 17: 1109-1111, 1999.

The assay of the present invention may be automated or semi-automated for high throughput screening or for screening for a number of immune effectors from the one subject. The automation is conveniently controlled by computer software.

The present invention contemplates a computer program product, therefore, for assessing the presence or absence or the level of one or more immune effectors, said product comprising:—

(1) code that receives, as input values, the identity of a reporter molecule associated with a labeled mRNA or antibody:

(2) code that compares said input values with reference values to determine the level of reporter molecules and/or the identity of the molecule to which the reporter molecule is attached; and (3) a computer readable medium that stores the codes.

In another embodiment, the program product further comprises code that receives as input information concerning the height of the sample in the test tube. In some embodiments, the information identifies a test vessel comprising a sample which has a shape that falls outside one or more pre-determined dimensions. In some embodiments, information may be in the form of a signal that reports the detection of a sample (and the corresponding test vessel) in which the height of the sample exceeds at least about 12 mm or other value corrected for different samples. In another embodiment, information may be in the form of a signal that reports the detection of a sample in which the height of the sample is less than about 6 mm or other value corrected for different samples.

Still another aspect of the present invention extends to a computer for assessing the presence or absence or level of one or more immune effectors, said computer comprises:—

(1) a machine-readable data storage medium comprising a data storage material encoded with machine-readable data, wherein said machine-readable data comprise input values which identify a reporter molecule associated with a labeled mRNA or antibody;

(2) a working memory for storing instructions for processing said machine-readable data;

(3) a central-processing unit coupled to said working memory and to said machine-readable data storage medium, for processing said machine readable data to compare said values to provide an assessment of the identity or level of reporter molecules or of molecules to which they are attached; and (4) an output hardware coupled to said central processing unit, for receiving the results of the comparison.

A version of these embodiments is presented in FIG. 1, which shows a system 10 including a computer 11 comprising a central processing unit ("CPU") 20, a working memory 22 which may be, e.g. RAM (random-access memory) or "core" memory, mass storage memory 24 (such as one or more disk drives or CD-ROM drives), one or more cathode-ray vessel ("CRT") display terminals 26, one or more keyboards 28, one or more input lines 30, and one or more output lines 40, all of which are interconnected by a conventional bidirectional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD. Alternatively, ROM drives or disk drives 24 in conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a synthetic polynucleotide sequence or a synthetic polypeptide sequence as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22, and determines the sequence of data processing steps. A number of programs may be used to process the machine readable data of this invention. Exemplary programs may use, for example, the following steps:—
(1) inputting input values which identifies a reporter molecule associated with a labeled mRNA or antibody;
(2) assessing including comparing said input values with reference values to determine the level of reporter molecule and/or the identity of the molecule to which the reporter molecule is attached; and
(3) outputting the results of the assessment.

Figure 2:
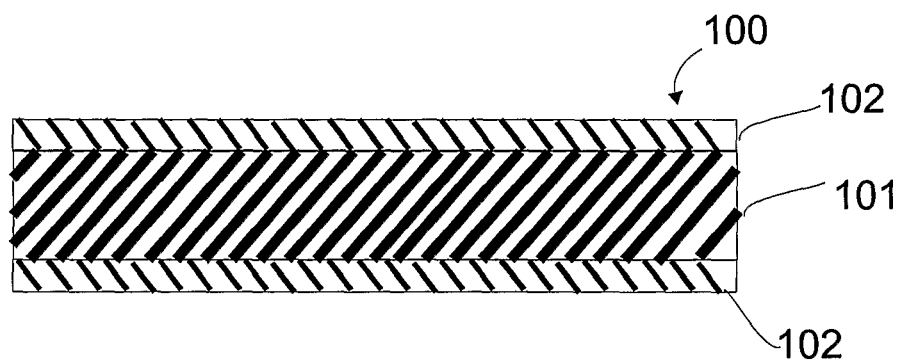
FIG. 2 is a diagrammatic representation of a cross-section of a magnetic storage medium.

FIG. 2 shows a cross section of a magnetic data storage medium 100 which can be encoded with machine readable data, or set of instructions, for assessing the level of an immune effector which can be carried out by a system such as system 10 of FIG. 1. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening for receiving the spindle of a disk drive or other data storage device 24. The magnetic domains of coating 102 of medium 100 are polarized or oriented so as to encode in manner which may be conventional, machine readable data for execution by a system such as system 10 of FIG. 1.

Figure 3:
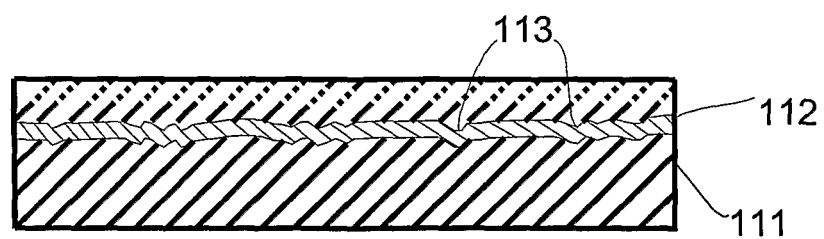
FIG. 3 is a diagrammatic representation of a cross-section of an optically readable data storage system.

FIG. 3 shows a cross section of an optically readable data storage medium 110 which also can be encoded with such a machine-readable data, or set of instructions, for designing a synthetic molecule of the invention, which can be carried out by a system such as system 10 of FIG. 1. Medium 110 can be a conventional compact disk read only memory (CD-ROM) or a rewritable medium such as a magneto-optical disk, which is optically readable and magneto-optically writable. Medium 100 preferably has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

The present invention further contemplates kits for assessing the capacity of a subject to mount a cell mediated response according to the methods described herein. The kit is conveniently in compartmental form with one or more compartments adapted to receive a sample from a subject such as whole blood preferably collected by capillary sampling, such as by a prick device. Thus in some embodiments, the kit comprises a device suitable for capillary sampling such as a device that punctures or perforates the skin to allow bleeding from peripheral capillaries. Containers for receiving a sample may have the same uniform dimensions or they may comprise a plurality of dimensions. In some embodiments, the containers for receiving samples are marked or otherwise arranged such that the height of the sample in the containers may be assessed. Containers may also be adapted to contain an anticoagulant where the sample is whole blood with or without a simple sugar, such as dextrose, to maintain the effective functional capacity of the immune cells.

Generally, the kit is in a form which is packaged for sale with a set of instructions. The instructions would generally be in the form of a method for measuring a CMI response in a subject, said method comprising collecting a sample from said subject wherein said sample comprises cells of the immune system which are capable of producing immune effector molecules following stimulation by an antigen, incubating said sample with an antigen under conditions in which the shape and the sample comprises a dimensions which has been optimised and then optionally measuring the presence or elevation in level of an immune effector molecule wherein the presence or level of said immune effector molecule is indicative of the capacity of said subject to mount a cell-mediated immune response.

Conveniently, the kit further comprises a capillary sampling device and/or an incubator. In some embodiments blood is collected using an about 3-4 mm diameter capillary tube.

In some embodiments, the subject from whom the sample is derived is a human subject such as a pediatric, adult or geriatric subject. Any animal or bird may be a subject.

Although the illustrated immune effector molecule is IFN-γ, other cytokines such as TNFα and GM-CSF a readily assayed, as are components of the complement system, perforins, defensins, cathelicidins, granzymes, Fas ligand, CD-40 ligand, exotaxin, cytotoxins, chemokines or monokines. In some embodiments the immune cells tested are selected from a natural killer (NK) cell, T-cell, B-cell, macrophage or monocyte.

In some embodiments the kit comprises an antigen is selected from a self-antigen, an antigen from a pathogenic organism, a metal or inorganic antigen, or a tumour antigen or an analog thereof. In some embodiments, the antigen is from Mycobacterium such as but in no way limited to ESAT-6, CFP-10 and TB7. In other embodiments, the antigen tested is tetanus toxoid (TT) or purified protein derivative (PPD) from *M. tuberculosis* or *M. avium*.

As described in relation to the method, the container is selected to provide the optimum sample shape during the incubation step. In some embodiments, the incubation container forms a sample height of at least about 4 mm to 6 mm to a maximum height of about 12 mm to 20 mm. In other embodiments, a sample height of at least about 6 mm to a maximum of about 12 mm is preferred. In some embodiments, the incubation container forms a sample height of 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm or 20 mm or an intervening height. In other embodiments, the incubation container forms a sample height of 6 mm, 7 mm, 8 mm, 9 mm, 10 mm, 11 mm or 12 mm or an intermediate height. In relation to the volume of sample in the incubation container, in some embodiments, the incubated sample has a volume of less than 500 μl, less than 400 μl, less than 300 μl, less than 200 μl, less than 100 μl, or less than 50 μl. In other embodiments, the sample is capillary blood and the incubated sample has a volume of about 2000 μl, 1500 μl, 1400 μl, 1300

μl, 1200 μl, 1100 μl, 900 μl, 800 μl, 700 μl, 600 μl, 500 μl, 400 μl, 300 μl, 200 μl, 100 μl, 50 μl or 40 μl or an intermediate volume.

In some embodiments, the kit comprises reagents for detecting IFN-γ and these include an antibody conjugate for detecting IFN-γ.

The present invention further provides a method of treatment of a subject having a pathogenic infection, an autoimmune disorder or cancer or a propensity for developing such a disorder, said method comprising assessing the ability of said subject to mount a cell mediated immune response by the method of measuring a CMI response in a subject, said method comprising collecting a sample from said subject optionally by capillary sampling wherein said sample comprises cells of the immune system which are capable of producing immune effector molecules following stimulation by an antigen, incubating said sample in an incubation container with an antigen under conditions in which the shape of the sample comprises a dimension which has been optimised and then measuring the presence of or elevation in the level of an immune effector molecule wherein the presence or level of said immune effector molecule is indicative of the capacity of said subject to mount a cell-mediated immune response and then selecting a suitable therapeutic protocol. In some embodiments, the sample is a blood sample. In some embodiments, the shape of the sample comprises a height of at least 6 mm to a maximum of about 12 mm. In other embodiments, the sample volume is less than 1 mL, even preferably less than 0.5 mL including 0.01 mL samples. In some embodiments, the subject is a livestock animal or human or avian subject. In further embodiments, the incubation container is suitable for maintaining an optimal shape of the sample, wherein the shape has one or two or more dimensions selected from: (i) a maximum circular diameter of less than 6 mm; (ii) a height of at least about 4 mm to 6 mm to a maximum height of about 12 mm to 20 mm; or (iii) a volume of less than 0.5 mL and optionally less than 400 μl.

In another aspect, the present invention provides a method for optimising an in vitro cellular immune response, the method comprising: i) incubating a plurality of cellular samples having a range of different heights or other dimensions in incubation containers wherein the cellular sample comprises cells that secrete an immune effector molecule following stimulation by an agent (such as an antigen, hapten or mitogen) with the agent in vitro for a time and under conditions sufficient for the cells to secrete the immune effector molecule; and ii) measuring the presence or level of the immune effector molecule from each sample; and iii) identifying the sample dimension that provides the optimal cellular response. In some embodiments, the dimension is the height of the sample in the incubating vessel. In another embodiment, the dimension is the volume of the sample in the incubating vessel. In other embodiments, the dimension is the maximum circular diameter of the sample in the incubation container.

The present invention is further described by the following non-limiting Examples.

Example 1

Detection of Immune Effector Molecule in Small Volumes of Sample Incubated with Antigen Whole blood from healthy donors (four donors) was collected into 9 mL Vacuette Li-heparin tubes having a cylindrical shape with 6.6 mm diameter and a U-shaped base. Aliquots of 0.1, 0.2, 0.3, 0.4 and 0.5 mL of blood were stimulated in Vacuette Mini-Collect tubes (no-additive). Blood was stimulated using Tetanus Toxoid and Phytohaemagglutinin-P (Mitogen). The volume of antigen added to each tube was proportional to the blood volume e.g., 0.1 mL blood was stimulated with 0.01 mL antigen; 0.4 mL of blood was stimulated with 0.04 mL antigen.

The IFN-γ responses generated in small volumes of blood were compared with responses generated using 1 mL of blood in a 13/75 Vacuette blood collection tube (Control).

Blood was incubated with antigen for between 16 and 24 hours at 37° C. before the plasma was removed for IFN-γ detection (QuantiFERON-TB Gold ELISA). Only 25 μL of plasma was assayed for the 0.1 mL samples due to insufficient sample being obtained.

ELISA testing demonstrated that IFN-γ was produced in volumes of blood as little as 0.1 mL (see Table 3). Within the 6.6 mm diameter vessel results for 0.3-0.4 mL blood in response to antigen were similar to the 1 mL control for each subject in a 11 mm diameter round vessel. Mitogen results were less affected by volumes and were similar from 0.1 mL to 0.5 mL indicating less need to optimise the volume with the container proportions.

In accordance with the present invention optimal cellular responses as measured by cytokine production or further effector mechanisms can be achieved in small volumes (such as those obtainable by prick sampling) as long as pre-optimisation of the vessel is performed; once it is realised this is possible, the optimisation can be done by one skilled in the art.

Example 2

Detection of Immune Effector Molecule in Small Volume of Whole Blood Incubated in Containers Having Different Internal Shapes Heparinised blood was dispensed into 3×5 mL aliquots in polypropylene tubes. Antigen, either human cytomegalovirus (CMV) or tetanus toxoid (tetanus) was added to the blood at appropriate concentrations. Each tube was mixed thoroughly and the blood (50 μl) dispensed into various containers where the volume of blood assumed different heights. Specifically, PCR tubes (conical to 10 mm height with maximum diameter 5 mm, u-shaped base), minicollect vessels (cylindrical with 6.5 mm diameter, u-shaped based), 96-well plate (cylindrical with 6.5 mm, diameter flat base) and 48-well plate (cylindrical with 11 mm diameter, flat base). The containers were incubated for 20 hours at 37° C. prior to removing plasma (20 μl) for testing by QFT-ELISA which detects the production of IFN-γ using a labelled antibody. In a control experiment, 1 mL of blood was incubated in a cylindrical container (internal diameter of 10.5 mm, flat base) and 20 μl of plasma tested by QFT-ELISA. The results are shown in Table 4 where IFN-γ in IU/mL are shown for nil antigen (Nil), tetanus toxoid (TT) and cytomegalovirus (CMV). Responses of 0.20 IU/mL and above Nil are significant. The height of the blood volume and the maximum circular diameter in the different containers is also shown in the Table 4. Strong signal are detected in subjects 1, 3, 4 and 5 with CMV and/or TT for sample heights of 11.5 mm and 6 mm. The signal drops off for CMV as the height goes below 6 mm to 3 mm and then 1.5 mm. Accordingly, a 15 μl whole blood sample provides a strong signal provided this volume of blood is incubated in an appropriate container providing a sample height of at least about 4 mm.

Example 3

Detection of Immune Effector Molecule in Peripheral Capillary Blood

Capillary blood was collected (150 µl) by finger prick into a lithium heparin minicollect tube. Small volume (50 µl) were transferred into three PCR tubes. The PCR tubes were conical having a cylindrical upper portion tapering over 10 mm to a conical base. Antigen being CMV or tetanus toxoid (Tetanus) or no antigen (Nil) were added to the tubes which were incubated for 20 hours at 37° C. Thereafter, plasma (20 µl) was removed and tested using QFT-ELISA. As shown in Table 5, the positive CMV control subject (TR) sample generated a significant signal compared to negative controls indicating that the assay can be conducted with volumes as small as 500 of capillary blood.

Example 4

Detection of Immune Effector Molecules Down to 6 mm Height and Up to 18 mm Height Heparinised human blood of different volumes was incubated with antigen (no antigen (Nil), tetanus toxoid (TT) or cytomegalovirus (CMV)) in three types of container providing a blood height of 11.5 mm, 18 mm and 6 mm. Plasma was tested in QFT-ELISA. The results (see Table 6) again show efficacy down to 6 mm. The results also show positive results with the 18 mm conical tube indicating that immune effector molecule are produced at sample heights of above 18 mm however optimum results are achieved between 5 and 18 mm.

The results shown in FIG. 3 were retabulated in Table 8 also providing the heights of the various blood samples. Here it can be seen that a reduced signal is produced as sample height increases from 16 mm upwards. The mitogen results have been removed from Table 3 in Table 8 because PHA-P is a non-specific stimulant whereas tetanus toxoid requires cellular antigen processing and presentation.

Example 5

Detection of Immune Effector Molecule Down to 4 mm and 20 µl of Whole Blood

Heparinised human blood of different volumes: 50 µl, 40 µl, 30 µl, 20 µl and 10 µl were tested in small PCR tubes providing sample heights of 6 mm, 5.5 mm, 5 mm, 4 mm and 2.5 mm, respectively. Antigens were: no antigen (N) tetanus toxoid (TT) and cytomegalovirus (CMV) at appropriate concentration. Blood was incubated at 37° C. for 20 hours and plasma removed for testing by QFT-ELISA. A control experiment (Table 7 Continued) using 1 mL cultures used small volumes of plasma (50 µl, 40 µl, 30 µl, 20 µl, 15 µl, 10 µl and 5 µl) to test by QFT-ELISA. The results shown in Table 7 show a positive signal down to 20 µl of blood with a height of 4 mm although optimum results were found at 5.5 and 6 mm.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

| List of suitable fluorophores | | |
|---|---|---|
| Probe | Ex$^1$ (nm) | Em$^2$ (nm) |
| Reactive and conjugated probes | | |
| Hydroxycoumarin | 325 | 386 |
| Aminocoumarin | 350 | 455 |
| Methoxycoumarin | 360 | 410 |
| Cascade Blue | 375; 400 | 423 |
| Lucifer Yellow | 425 | 528 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| APC-Cy7 conjugates | 650; 755 | 767 |
| Red 613 | 480; 565 | 613 |
| Fluorescein | 495 | 519 |
| FluorX | 494 | 520 |
| BODIPY-FL | 503 | 512 |
| TRITC | 547 | 574 |
| X-Rhodamine | 570 | 576 |
| Lissamine Rhodamine B | 570 | 590 |
| PerCP | 490 | 675 |
| Texas Red | 589 | 615 |
| Allophycocyanin (APC) | 650 | 660 |
| TruRed | 490, 675 | 695 |
| Alexa Fluor 350 | 346 | 445 |
| Alexa Fluor 430 | 430 | 545 |
| Alexa Fluor 488 | 494 | 517 |
| Alexa Fluor 532 | 530 | 555 |
| Alexa Fluor 546 | 556 | 573 |
| Alexa Fluor 555 | 556 | 573 |
| Alexa Fluor 568 | 578 | 603 |
| Alexa Fluor 594 | 590 | 617 |
| Alexa Fluor 633 | 621 | 639 |
| Alexa Fluor 647 | 650 | 688 |
| Alexa Fluor 660 | 663 | 690 |
| Alexa Fluor 680 | 679 | 702 |
| Alexa Fluor 700 | 696 | 719 |
| Alexa Fluor 750 | 752 | 779 |
| Cy2 | 489 | 506 |
| Cy3 | (512); 550 | 570; (615) |
| Cy3, 5 | 581 | 596; (640) |
| Cy5 | (625); 650 | 670 |
| Cy5, 5 | 675 | 694 |
| Cy7 | 743 | 767 |
| Nucleic acid probes | | |
| Hoechst 33342 | 343 | 483 |
| DAPI | 345 | 455 |
| Hoechst 33258 | 345 | 478 |
| SYTOX Blue | 431 | 480 |
| Chromomycin A3 | 445 | 575 |
| Mithramycin | 445 | 575 |
| YOYO-1 | 491 | 509 |
| SYTOX Green | 504 | 523 |
| SYTOX Orange | 547 | 570 |
| Ethidium Bormide | 493 | 620 |
| 7-AAD | 546 | 647 |
| Acridine Orange | 503 | 530/640 |
| TOTO-1, TO-PRO-1 | 509 | 533 |
| Thiazole Orange | 510 | 530 |
| Propidium Iodide (PI) | 536 | 617 |
| TOTO-3, TO-PRO-3 | 642 | 661 |
| LDS 751 | 543; 590 | 712; 607 |
| Fluorescent Proteins | | |
| Y66F | 360 | 508 |
| Y66H | 360 | 442 |
| EBFP | 380 | 440 |
| Wild-type | 396, 475 | 50, 503 |
| GFPuv | 385 | 508 |
| ECFP | 434 | 477 |

TABLE 1-continued

List of suitable fluorophores

| Probe | Ex[1] (nm) | Em[2] (nm) |
|---|---|---|
| Y66W | 436 | 485 |
| S65A | 471 | 504 |
| S65C | 479 | 507 |
| S65L | 484 | 510 |
| S65T | 488 | 511 |
| EGFP | 489 | 508 |
| EYFP | 514 | 527 |
| DsRed | 558 | 583 |
| Other probes | | |
| Monochlorobimane | 380 | 461 |
| Calcein | 496 | 517 |

[1]Ex: Peak excitation wavelength (nm)
[2]Em: Peak emission wavelength (nm)

TABLE 2

Exemplary optical parameters which may be measured by a flow cytometer.

| Parameter | Acronym | Detection angle form incident laser beam | Wavelength (nm) |
|---|---|---|---|
| Forward scattered light | FS | 2-5° | 488* |
| Side scattered light | SS | 90° | 488* |
| "Green" fluorescence | FL1 | 90° | 510-540† |
| "Yellow" fluorescence | FL2 | 90° | 560-580† |
| "Red" fluorescence | FL3 | 90° | >650# |

*using a 488 nm excitation laser
†width of bandpass filter
longpass filter

TABLE 3

Optimisation of small vessel for blood stimulation (6.6 mm internal diameter)

| Blood Volume (mL) | Subject 1 | | | Subject 2 | | | Subject 3 | | | Subject 4 | | |
|---|---|---|---|---|---|---|---|---|---|---|---|---|
| | Nil | TT | Mit | Nil | TT | Mit | Nil | TT | Mit | Nil | TT | Mit |
| 0.1 | 0.11# | 1.31# | 2.44# | 0.37# | 4.2# | 42.57*# | 0.21# | 0.17# | 13.93# | 0.08# | 0.99# | 40.39*# |
| 0.2 | 0.16 | 4.88 | 3.82 | 0.06 | 24.03 | 42.57* | 0.14 | 1.14 | 17.02 | 0.07 | 6.1 | 40.39* |
| 0.3 | 0.16 | 10.13 | 2.72 | 0.07 | 42.57* | 42.57* | 0.15 | 1.72 | 8.74 | 0.08 | 14.37 | 40.39* |
| 0.4 | 0.15 | 10.45 | 3.29 | 0.05 | 42.57* | 42.57* | 0.12 | 4.01 | 8.82 | 0.08 | 12.11 | 40.39* |
| 0.5 | 0.19 | 3.29 | 3.11 | 0.18 | 42.57* | 42.57* | 0.11 | 3.15 | 12.21 | 0.08 | 6.36 | 40.39* |
| Control | 0.32 | 11.51 | 4.91 | 1.51 | 42.57* | 42.57* | 0.24 | 4.37 | 19.93 | 0.09 | 9.01 | 40.39* |

Nil = PBS alone,
TT = Tetanus Toxoid,
Mit = Mitogen (PHA-P)
*= Off-scale result
= Only 25 μL of plasma was available for testing (corrected result 2X shown)

TABLE 4

| Subject | Antigen | PCR Tube (50 μl culture, 20 μl in EIA) Conical to 10 mm height with maximum diameter of 5 mm, u-shaped base Blood Height = 6 mm | MiniCollect (50 μl culture, 20 μl in EIA) Cylindrical with 6.5 mm diameter, u-shaped base Blood Height = 3 mm | 96 well plate (50 μl culture, 20 μl in EIA) Cylindrical with 6.5 mm diameter, flat base Blood Height = 1.5 mm | 48 well plate (50 μl culture, 20 μl in EIA) Cylindrical with 11 mm diameter, flat base Blood Height = 0.5 mm | Control (1 mL culture, 50 μl in EIA) Cylindrical with 10.5 mm diameter, flat base (gel) Blood height = 11.5 mm | Control (1 mL culture, 20 μl in EIA) |
|---|---|---|---|---|---|---|---|
| 1 | Nil | 0.13 | 0.03 | 0.87 | 0.06 | 0.02 | 0.02 |
| | TT | 5.82 | 4.26 | 0.39 | 0.39 | 12.16 | 12.16 |
| | CMV | 3.72 | 1.99 | 1.07 | 0.97 | 6.24 | 3.92 |
| 2 | Nil | 0.07 | 0.02 | 0.05 | 0.04 | 0.02 | 0.02 |
| | TT | 0.34 | 0.96 | 0.15 | 0.27 | 1.30 | 0.81 |
| | CMV | 0.05 | 0.02 | 0.05 | 0.05 | 0.02 | 0.02 |
| 3 | Nil | 0.09 | 0.02 | 0.05 | 0.05 | 0.03 | 0.02 |
| | TT | 12.16 | 12.16 | 12.16 | 12.16 | 12.16 | 12.16 |
| | CMV | 7.38 | 1.31 | 0.69 | 0.56 | 12.16 | 7.83 |
| 4 | Nil | 0.14 | 0.05 | 0.10 | 0.07 | 0.05 | 0.04 |
| | TT | 0.86 | 0.44 | 0.37 | 0.21 | 5.31 | 3.26 |
| | CMV | 0.07 | 0.05 | 0.12 | 0.06 | 0.05 | 0.04 |
| 5 | Nil | 0.08 | 0.07 | 5.50 | 0.11 | 0.03 | 0.04 |
| | TT | 2.34 | 0.58 | 0.18 | 0.15 | 7.87 | 5.00 |
| | CMV | 0.22 | 0.10 | 0.11 | 0.12 | 0.12 | 0.11 |

Comparison is with 1 mL using 20 μl of plasma.
IFN-gamma in IU/mL in response to Nil,
CMV Antigen or Tetanus Toxoid results shown.

TABLE 5

Capillary Blood

| Subject | IFN-gamma (IU/mL) Nil | CMV | Tetanus |
|---|---|---|---|
| TR | 0.22 | 27.07 | — |
| JH | 0.12 | — | 0.4 |

TABLE 6

Varied Volume of Culture in PCR Tubes
IFN-gamma in IU/mL in response to Nil, CMV Antigen or Tetanus Toxoid results shown

| Subject | Antigen | 1 mL control Cylindrical 11.5 mm blood height | 300 μl Conical* 18 mm blood height | 50 μl Conical* 6 mm blood height |
|---|---|---|---|---|
| 1 | N | 0.10 | 0.11 | 0.17 |
|   | TT | 5.51 | 3.99 | 4.66 |
|   | CMV | 2.68 | 2.98 | 1.84 |

TABLE 6-continued

Varied Volume of Culture in PCR Tubes
IFN-gamma in IU/mL in response to Nil, CMV Antigen or Tetanus Toxoid results shown

| Subject | Antigen | 1 mL control Cylindrical 11.5 mm blood height | 300 μl Conical* 18 mm blood height | 50 μl Conical* 6 mm blood height |
|---|---|---|---|---|
| 2 | N | 0.11 | 0.12 | 0.06 |
|   | TT | 0.35 | 0.49 | 0.70 |
|   | CMV | 0.11 | 0.10 | 0.12 |
| 3 | N | 0.07 | 0.10 | 0.08 |
|   | TT | 13.81 | 13.07 | 9.28 |
|   | CMV | 3.00 | 3.93 | 1.79 |
| 4 | N | 0.05 | 0.10 | 0.08 |
|   | TT | 1.09 | 1.16 | 0.60 |
|   | CMV | 0.08 | 0.10 | 0.10 |
| 5 | N | 0.04 | 0.04 | 0.06 |
|   | TT | 0.54 | 0.21 | 0.14 |
|   | CMV | 0.07 | 0.06 | 0.07 |

20 μl plasma assayed in each case
Shows efficacy down to 6 mm height and 50 μl
*Tubes taper up to 10 mm height and then are cylindrical to 20 mm height. Diameter of tube at cyclindrical section is 5 mm.

TABLE 7

Varied Low Volume Culture
IFN-gamma in IU/mL in response to Nil, CMV Antigen or Tetanus Toxoid results shown PCR Tubes (conical to 10 mm height with maximum diameter of 5 mm)

| Subject | Antigen | 50 μl culture (25 μl Plasma in EIA) Blood height = 6 mm | 40 μl culture (20 μl Plasma in EIA) Blood height = 5.5 mm | 30 μl culture (15 μl Plasma in EIA) Blood height = 5 mm | 20 μl culture (10 μl Plasma in EIA) Blood height = 4 mm | 10 μl culture (5 μl Plasma in EIA) Blood height = 2.5 mm |
|---|---|---|---|---|---|---|
| 1 | N | 0.14 | 0.07 | 0.04 | 0.05 | 0.05 |
|   | TT | 6.05 | 5.96 | 3.62 | 1.98 | 0.08 |
|   | CMV | 3.37 | 3.59 | 1.79 | 1.22 | 1.11 |
| 2 | N | 0.04 | 0.05 | 0.12 | 0.05 | 0.13 |
|   | TT | 1.82 | 0.25 | 0.30 | 0.23 | 0.13 |
|   | CMV | 0.04 | 0.05 | 0.06 | 0.05 | 0.07 |
| 3 | N | 0.05 | 0.05 | 0.06 | 0.02 | 2.52 |
|   | TT | 14.28 | 14.28 | 9.97 | 2.04 | 0.41 |
|   | CMV | 2.39 | 2.75 | 0.39 | 0.74 | 0.26 |
| 4 | N | 0.09 | 0.07 | 0.07 | 0.06 | 0.06 |
|   | TT | 0.25 | 0.47 | 0.36 | 0.08 | 0.09 |
|   | CMV | 0.07 | 0.07 | 0.08 | 0.07 | 0.10 |
| 5 | N | 0.06 | 0.04 | 0.06 | 0.03 | 0.05 |
|   | TT | 0.49 | 0.48 | 0.16 | 0.09 | 0.04 |
|   | CMV | 0.04 | 0.06 | 0.04 | 0.02 | 0.04 |

1 mL Control (cylindrical with 10.5 mm diameter)

| Subject | Antigen | 1 mL culture (50 μl Plasma in EIA) | 1 mL culture (40 μl Plasma in EIA) | 1 mL culture (30 μl Plasma in EIA) | 1 mL culture (25 μl Plasma in EIA) | 1 mL culture (20 μl Plasma in EIA) | 1 mL culture (15 μl Plasma in EIA) | 1 mL culture (10 μl Plasma in EIA) | 1 mL culture (5 μl Plasma in EIA) |
|---|---|---|---|---|---|---|---|---|---|
|   |   | Blood height = 11.5 mm | | | | | | | |
| 1 | N | 0.02 | 0.02 | 0.02 | 0.02 | 0.02 | 0.02 | 0.02 | 0.03 |
|   | TT | 13.48 | 13.48 | 13.48 | 13.48 | 13.48 | 8.05 | 6.04 | 3.40 |
|   | CMV | 8.04 | 7.40 | 6.59 | 5.72 | 4.64 | 4.19 | 2.82 | 1.99 |
| 2 | N | 0.02 | 0.02 | 0.02 | 0.02 | 0.03 | 0.02 | 0.03 | 0.04 |
|   | TT | 0.95 | 0.80 | 0.67 | 0.58 | 0.52 | 0.45 | 0.35 | 0.33 |
|   | CMV | 0.02 | 0.02 | 0.02 | 0.02 | 0.02 | 0.03 | 0.03 | 0.04 |
| 3 | N | 0.02 | 0.02 | 0.02 | 0.02 | 0.02 | 0.02 | 0.02 | 0.03 |
|   | TT | 14.28 | 14.28 | 14.28 | 14.28 | 14.28 | 14.28 | 14.28 | 14.28 |
|   | CMV | 9.16 | 6.97 | 6.36 | 6 | 5.3 | 4.84 | 3.77 | 2.13 |

TABLE 7-continued

Varied Low Volume Culture
IFN-gamma in IU/mL in response to Nil, CMV Antigen or Tetanus Toxoid results shown

| 4 | N   | 0.05 | 0.05 | 0.04 | 0.04 | 0.04 | 0.04 | 0.04 | 0.04 |
|---|-----|------|------|------|------|------|------|------|------|
|   | TT  | 3.98 | 3.49 | 3.02 | 2.43 | 2.07 | 1.69 | 1.17 | 0.08 |
|   | CMV | 0.04 | 0.04 | 0.03 | 0.03 | 0.03 | 0.03 | 0.03 | 0.04 |
| 5 | N   | 0.03 | 0.03 | 0.03 | 0.03 | 0.03 | 0.02 | 0.03 | 0.02 |
|   | TT  | 0.98 | 0.9  | 0.79 | 0.69 | 0.59 | 0.47 | 0.37 | 0.22 |
|   | CMV | 0.08 | 0.08 | 0.07 | 0.07 | 0.07 | 0.06 | 0.05 | 0.04 |

TABLE 8

Varied Volume of Culture in Minicollect (R)Tubes (Greiner Bio-One)

| | | Blood height | | | | |
|---|---|---|---|---|---|---|
| Subject | Antigen | 100 µl (25 µl assayed) | 200 µl | 300 µl | 400 µl | 500 µl | 1 mL control (50 µl assayed) |
| | | 4 mm | 8 mm | 12 mm | 16 mm | 20 mm | |
| 1 | N  | 0.11 | 0.16  | 0.16   | 0.15   | 0.19 | 0.32 |
|   | TT | 1.31 | 4.88  | 10.13  | 10.45  | 3.29 | 11.51 |
| 2 | N  | 0.37 | 0.06  | 0.07   | 0.05   | 0.18 | 1.51 |
|   | TT | 4.20 | 24.03 | 42.57* | 42.57  | 42.57 | 42.57 |
| 3 | N  | 0.21 | 0.14  | 0.15   | 0.12   | 0.11 | 0.24 |
|   | TT | 0.17 | 1.14  | 1.72   | 4.01   | 3.15 | 4.37 |
| 4 | N  | 0.08 | 0.07  | 0.08   | 0.08   | 0.11 | 0.05 |
|   | TT | 0.99 | 6.10  | 14.37  | 12.11  | 6.36 | 1.09 |

*indicates maximum for that run, real value is >
▒ Indicates maximum values obtained with protein antigen (excluding control)
N = Nil, TT = tetanus toxoid added

BIBLIOGRAPHY

Altschul et al., *Nucl. Acids Res.*, 25:3389, 1997.
Ausubel et al., *Current Protocols in Molecular Biology* John Wiley & Sons Inc, 1994-1998, Chapter 15.
Ausubel (Ed) *Current Protocols in Molecular Biology*, 5$^{th}$ Edition, John Wiley & Sons, Inc, NY, 2002.
Biggs et al., *Cytometry*, 36:36-45, 1999.
Bonner et al., *Eur. J. Biochem.*, 46:83, 1974.
Brock et al., *Int. J. Tuberc. Lung. Dis*, 5(5):462-467, 2001.
Daneshvar et al., *J. Immunol. Methods*, 226(1-2):119-128, 1999.
Durig et al., *J. Raman Spectrosc.*, 24(5):281-285, 1993.
Eriksson et al., *Biophys. J.*, 2:64, 1993.
Erickson et al., *Science*, 249:527-533, 1990.
Fu et al., *Nature Biotechnology*, 17: 1109-1111, 1999.
Hodgson, *Bio/Technology*, 9:19-21, 1991.
Kurrek, *Eur. J. Biochem.*, 270:1628-1644, 2003.
Lakowicz et al., *Biophys. J.*, 72: 567, 1997.
Lewis et al., *Dyes Pigm.*, 42(2):197, 1999.
Malemed et al., "*Flow cytometry and sorting*", 2$^{nd}$ Ed., New York, Wiley-Liss, 1990.
Marmur et al., *J. Mol. Biol.*, 5:109, 1962.
Rahman et al., *J. Org. Chem.*, 63:6196, 1998.
Rapaport et al., *Appl. Phys. Lett.*, 74(3):329-331, 1999.
Remington's Pharmaceutical Sciences, 18$^{th}$ Ed., 1990, Mack Publishing, Company, Easton, Pa., U.S.A.
Sambrook, *Molecular Cloning: A Laboratory Manual*, 3$^{rd}$ Edition, CSHLP, CSH, NY, 2001.
Skjot et al., *Infection and Immunity*, 68(1):214-20, 2000.
Summerton et al., *Antisense and Nucleic acid Drug Development*, 7:187-195, 1997.
Tawa et al., *Mater. Res. Soc. Symp. Proc.*, 488 [Electrical, Optical and Magnetic Properties of Organic Solid-State Materials IV], 885-890.
Wells, *Methods Enzymol.*, 202:2699-2705, 1991.
Youvan et al., *Biotechnology.* 3:1-18, 1997.

The invention claimed is:

1. A method for measuring a cell-mediated immune (CMI) response in a sample of whole blood collected from a subject to determine a capacity of the subject to mount a CMI response, comprising:
   a) incubating an antigen in an incubation container with an undiluted whole blood sample from a peripheral capillary of the subject or from an artery or vein of the subject, wherein the whole blood sample comprises immune system cells which are capable of producing immune effector molecules following stimulation by the antigen,
      wherein in the incubation container the whole blood sample has a shape that has (i) a maximum circular diameter of less than 6 mm and (ii) a height of from at least 4 mm to 6 mm to a maximum height of 12 mm to 20 mm, and
      wherein the whole blood sample that is incubated has a total volume that is less than 500 µl; and
   b) subsequent to step (a) detecting, in the whole blood sample that has been incubated, a level of at least one immune effector molecule, or of a nucleic acid molecule capable of producing said at least one immune effector molecule, wherein the level of the at least one immune effector molecule, or of the nucleic acid molecule capable of producing said at least one immune effector molecule, is indicative of the capacity of the subject to mount a cell-mediated response.

2. The method of claim 1 further comprising a step of selecting a therapeutic protocol for treatment of a subject having symptoms of a disorder that is selected from an inflammatory disease condition, a pathogenic infection, an autoimmune disorder, immuno-incompetence, allergy and cancer, or having a propensity for developing such a disorder.

3. The method of claim 1 or claim 2 wherein the sample of whole blood is collected (i) with a capillary sampling device, (ii) into a container containing either or both of the antigen and an anti-coagulant, or (iii) into a container to which either or both of the and an anti-coagulant are added thereafter.

4. The method of claim 3, wherein the anti-coagulant is heparin.

5. The method of claim 1 or claim 2 wherein a simple sugar is present in the incubation container during the step of incubating.

6. The method of claim 5 wherein the simple sugar is dextrose.

7. The method of claim 1 or claim 2 wherein the step of incubating comprises incubating for from 4 hours to 50 hours.

8. The method of claim 1 or claim 2 wherein:
a) the total volume of the whole blood sample is less than 400 µl, less than 300 µl, less than 200 µl, less than 100 µl, or less than 50 µl, or
b) the whole blood sample is from a peripheral capillary of the subject and the total volume is about 400 µl, 300 µl, 200 µl, 100 µl, 50 µl or 40 µl or an intermediate volume therebetween.

9. The method of claim 1 or claim 2 which is selected from:
(a) a method that further comprises (i) mixing the sample of whole blood in the incubation container; (ii) centrifuging the incubation container and collecting plasma; and (iii) detecting an immune effector molecule in the plasma, and
(b) a method that further comprises (i) mixing the sample of whole blood in the incubation container; (ii) including in the incubation container during the step of incubating at least one of a control antigen and a mitogen; (iii) centrifuging the incubation container and collecting plasma; and (iv) detecting an immune effector molecule in the plasma.

10. The method of claim 9 wherein the sample of whole blood is collected from the subject into a 3-4 mm diameter capillary tube.

11. The method of claim 1 or 2 wherein the shape of the whole blood sample in the incubation container has a volume of less than 400 µl.

\* \* \* \* \*